United States Patent [19]
Williams

[11] Patent Number: 6,119,029
[45] Date of Patent: Sep. 12, 2000

[54] AMBULATORY RECORDER HAVING SPLASH RESISTANT SENSOR PORTS

[75] Inventor: Malcolm G. S. Williams, Stockholm, Sweden

[73] Assignee: Medtronic, Inc., Minneapolis, Minn.

[21] Appl. No.: 09/129,918

[22] Filed: Aug. 6, 1998

[51] Int. Cl.⁷ ...................................................... A61B 5/05
[52] U.S. Cl. ........................... 600/361; 128/903; 600/343
[58] Field of Search .......................... 600/361, 300–301, 600/343, 436, 481–486, 500–508, 529–538; 128/900, 903, 904; 607/46

[56] References Cited

U.S. PATENT DOCUMENTS

| | | |
|---|---|---|
| D. 396,037 | 7/1998 | Cappa et al. . |
| 3,898,984 | 8/1975 | Mandel et al. . |
| 3,941,137 | 3/1976 | Vredenbregt et al. . |
| 4,003,379 | 1/1977 | Ellinwood, Jr. . |
| 4,082,084 | 4/1978 | Lipscher . |
| 4,129,125 | 12/1978 | Lester et al. . |
| 4,183,354 | 1/1980 | Sibley et al. . |
| 4,198,963 | 4/1980 | Barkalow et al. . |
| 4,333,475 | 6/1982 | Moreno et al. . |
| 4,353,375 | 10/1982 | Colburn et al. . |
| 4,365,636 | 12/1982 | Barker . |
| 4,370,983 | 2/1983 | Lichtenstein . |
| 4,464,172 | 8/1984 | Lichtenstein . |
| 4,503,859 | 3/1985 | Petty et al. . |
| 4,529,401 | 7/1985 | Leslie et al. . |
| 4,531,527 | 7/1985 | Reinhold, Jr. et al. . |
| 4,592,018 | 5/1986 | Wiegman . |
| 4,628,928 | 12/1986 | Lowell . |
| 4,632,119 | 12/1986 | Reichstein . |
| 4,667,682 | 5/1987 | Ihlenfeld, III . |
| 4,684,367 | 8/1987 | Schaffer et al. . |
| 4,715,385 | 12/1987 | Cudahy et al. . |
| 4,748,562 | 5/1988 | Miller et al. . |
| 4,771,772 | 9/1988 | DeWitt . |
| 4,774,956 | 10/1988 | Kruse et al. . |
| 4,794,934 | 1/1989 | Motoyama et al. . |
| 4,895,161 | 1/1990 | Cudahy et al. . |
| 4,900,305 | 2/1990 | Smith et al. . |
| 4,917,092 | 4/1990 | Todd et al. . |
| 4,974,599 | 12/1990 | Suzuki . |
| 5,002,062 | 3/1991 | Suzuki . |
| 5,007,427 | 4/1991 | Suzuki et al. .............................. 607/46 |
| 5,010,888 | 4/1991 | Jadvar et al. . |
| 5,012,411 | 4/1991 | Policastro et al. . |
| 5,016,636 | 5/1991 | Kulakowski . |
| 5,042,481 | 8/1991 | Suziki et al. . |
| 5,072,458 | 12/1991 | Suzuki . |
| 5,086,778 | 2/1992 | Mueller et al. . |
| 5,107,835 | 4/1992 | Thomas . |
| 5,111,396 | 5/1992 | Mills et al. . |
| 5,111,818 | 5/1992 | Suzuki et al. . |
| 5,113,869 | 5/1992 | Nappholz et al. . |
| 5,117,827 | 6/1992 | Stuebe et al. . |
| 5,131,816 | 7/1992 | Brown et al. . |
| 5,158,083 | 10/1992 | Sacristan et al. . |
| 5,188,104 | 2/1993 | Wernicke et al. . |
| 5,213,568 | 5/1993 | Lattin et al. . |
| 5,222,503 | 6/1993 | Ives et al. . |
| 5,224,485 | 7/1993 | Powers et al. . |
| 5,226,431 | 7/1993 | Bible et al. . |
| 5,228,450 | 7/1993 | Sellers . |
| 5,238,001 | 8/1993 | Gallant et al. . |
| 5,261,401 | 11/1993 | Baker et al. . |

(List continued on next page.)

FOREIGN PATENT DOCUMENTS 0 356 603   9/1988   Sweden .......................... A61B 5/04

*Primary Examiner*—Cary O'Connor
*Assistant Examiner*—Michael Astorino
*Attorney, Agent, or Firm*—Thomas F. Woods; Michael J. Jaro; Harold Patton

[57] ABSTRACT

An ambulatory device having a case with an integral splash cover about the area of the catheter input ports is described. Moreover, the ports are angled such that when the device is carried in its intended manner by a patient, the ports are angled downwards. Through the case design, in combination with the angle of the ports, the device is relatively more resistant to splash-related problems as compared to prior devices.

14 Claims, 5 Drawing Sheets

U.S. PATENT DOCUMENTS

| | | | |
|---|---|---|---|
| 5,263,491 | 11/1993 | Thornton . | |
| 5,273,033 | 12/1993 | Hoffman | 600/436 |
| 5,292,344 | 3/1994 | Douglas . | |
| 5,305,202 | 4/1994 | Gallant et al. . | |
| 5,305,761 | 4/1994 | Byrne et al. . | |
| 5,307,263 | 4/1994 | Brown . | |
| 5,309,920 | 5/1994 | Gallant et al. . | |
| 5,338,157 | 8/1994 | Blomquist . | |
| 5,341,291 | 8/1994 | Roizen et al. . | |
| 5,343,870 | 9/1994 | Gallant et al. . | |
| 5,355,892 | 10/1994 | Saltzstein . | |
| 5,368,562 | 11/1994 | Blomquist et al. . | |
| 5,381,351 | 1/1995 | Kwong et al. . | |
| 5,388,587 | 2/1995 | Knutsson et al. . | |
| 5,411,022 | 5/1995 | McCue et al. . | |
| 5,429,602 | 7/1995 | Hauser . | |
| 5,431,634 | 7/1995 | Brown . | |
| 5,432,698 | 7/1995 | Fujita . | |
| 5,438,985 | 8/1995 | Essen-Moller | 600/343 |
| 5,479,019 | 12/1995 | Gross . | |
| 5,479,935 | 1/1996 | Essen-Moller . | |
| 5,507,904 | 4/1996 | Fisher et al. . | |
| 5,526,809 | 6/1996 | Fiddian-Green . | |
| 5,545,183 | 8/1996 | Altman . | |
| 5,607,460 | 3/1997 | Kroll . | |
| 5,645,068 | 7/1997 | Mezack et al. . | |
| 5,657,759 | 8/1997 | Essen-Moller . | |
| 5,701,894 | 12/1997 | Cherry et al. . | |
| 5,704,368 | 1/1998 | Asano et al. . | |
| 5,704,890 | 1/1998 | Bliss et al. . | |
| 5,749,907 | 5/1998 | Mann . | |
| 5,873,369 | 2/1999 | Laniado et al. | 128/903 |

AMBULATORY RECORDER HAVING SPLASH RESISTANT SENSOR PORTS

FIELD OF THE INVENTION

The present invention relates to a method for ambulatory recording, for medical and especially for diagnostic purposes, by means of a portable recorder slidable patient activity period switch, the switch permitting a notation to be made in the recorded data upon the start of a pre-defined activity, e.g. smoking.

Ambulatory recording and recorders are widely used. Such devices include the Digitrapper Mk III™ ambulatory recorder from Synectics Medical AB, the GastroScan II™ from Medical Instruments Corporation, and the SuperLogger™ from Sandhill Scientific. These types of devices make it possible for patients to remain at home, or at the least be ambulant in a hospital setting while physiological data is recorded. Typically the devices comprise a lightweight recorder in which the desired physiological data signals are temporarily stored and later downloaded for future analysis.

Many types of physiological data may be recorded, including ECG data (Electrocardiogram), EEG data (Electroencephalogram) and pH or pressure data (Motility) in the gastrointestinal tract. Preferably such a recorder should be able to record among a programmable number of channels at a variety of programmable frequencies.

One problem often faced with designing ambulatory recorders lies in the fact that ambulatory medical recorders record data over a prolonged period of time, e.g. 24 hours. Regardless of the specific types of data to be collected, ambulatory devices must operate under a variety of demanding conditions. Sometimes these conditions include the exposure, by splash or otherwise, to liquids or bodily fluids (water or vomit, for example.) One area where this exposure can be most damaging is if the fluid enters into the device through one or more of the sensor ports, i.e. the catheter input. Because recorders typically are electrical devices, liquids or fluids within the device encasement can interfere with reliable operation. Moreover, fluid entering in the plug area may lead to erroneous data being registered.

SUMMARY OF THE INVENTION

An ambulatory device having a case with an integral splash cover about the area of the catheter input ports is described. Moreover, the ports are angled such that when the device is carried in its intended manner by a patient, the ports are angled downwards. Through the case design, in combination with the angle of the ports, the device is relatively more resistant to splash-related problems as compared to prior devices.

The Figures are not necessarily to scale.

DETAILED DESCRIPTION OF THE DRAWINGS

Figure 1A:
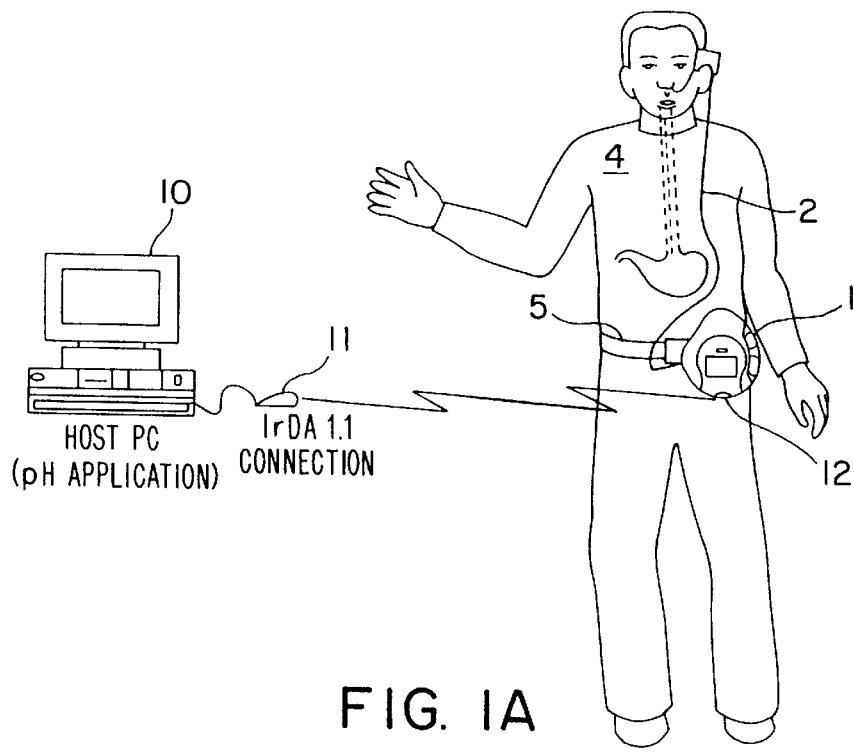
FIG. 1A depicts an ambulatory recorder of the present invention.

FIG. 1A depicts an ambulatory recorder of the present invention. As seen, ambulatory recorder 1 of the present invention may be carried by a patient. In the preferred embodiment, recorder 1 may be either carried through a mounting in the back of the recorder enclosure which fastens to patient's belt 5, or the same mounting may be coupled to be carried using a shoulder harness (not shown). Recorder 1 is coupled to patient 4 through one or more sensing catheters 2. Sensing catheters may be positioned in any area of the patient's body from which data is to be sensed, including the esophagus, as depicted in FIG. 1A. It should be noted the ambulatory recorder of the present invention may be used to collect many or various types of data including gastrointestinal (including pH and pressure) data, neurological data, as well as neuromuscular data, EEG data or EMG data.

Among the various sensing catheters which may be coupled to the device are manometry catheters and pH testing catheters, including the Synectics Medical AB, Stockholm, Sweden Model G 91-9 series of Multi use pH catheters; Synectics Medical AB Model G 91-2 series of Multi use pH catheters with perfusion port; or the Zinectics Inc., Salt Lake City, Utah disposable 24 pH catheter Model series G91-6 or G 91-7. While a single catheter 2 is shown depicted in this figure, recorder 1 further permits two separate sensors to be coupled to the device, as seen in FIG. 1B.

As further seen in this figure, the recorder may also communicate with a host PC 10 via an infra red data link facility through an IrDA connection 11 such as, for example, a JETEYE ESI-57680 available form Extended Systems, Inc., Boise, Id., which communicates with the recorder using the infra Red Data Association 1.1 Connection Protocol. As seen, infrared data connection makes a link to infra red port 12 on recorder 1.

Figure 1B:
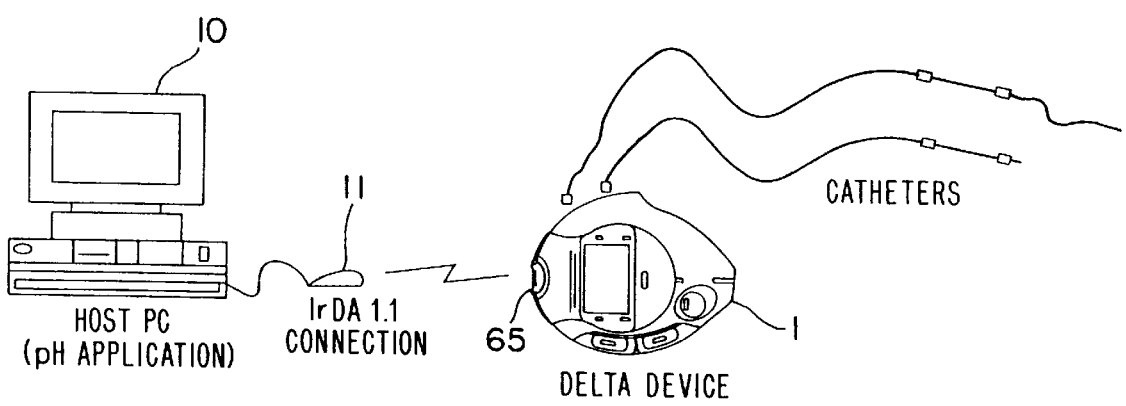
FIG. 1B illustrates a further manner in which the recorder 1 may also have an infra red data communication link established with a host PC.

FIG. 1B illustrates a further manner in which recorder 1 may also have an infra red data communication link established with a host PC. In particular, infra red data communication may be further established when the recorder is not worn by the patient. As discussed in more detail below, one of the advantages of the present invention is that the infra red data components and recorder case permit such a link to be made when the device is worn as shown in FIG. 1A, as well as when the device is removed from the patient and positioned in proximity to mouse 11.

Figure 2:
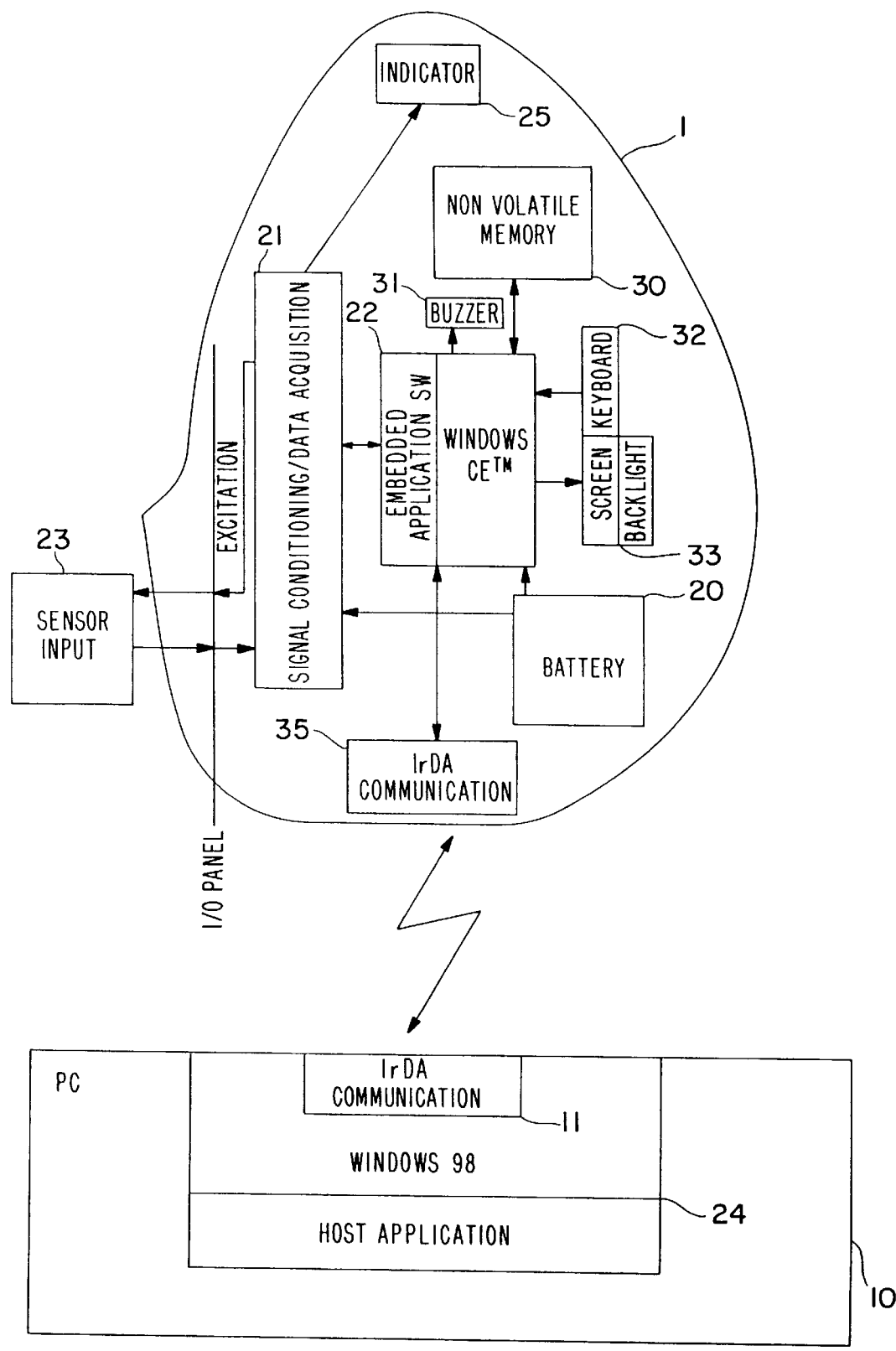
FIG. 2 is a block diagram of the data recording system shown in FIG. 1B.

FIG. 2 is a block diagram of the data recording system shown in FIG. 1B. As seen, recorder 1 features a battery 20 which is coupled to the signal conditioning/data acquisition block that is driven by real time processor 21. The battery is coupled as well as to non-real time processor 22 that runs the application. As disclosed in more detail below, real time processor 21 is a low power processor which is used to sample data received from sensor input 23 by a sensor attached thereto (not shown in this FIG. 2).

Sampling is achieved through the signal conditioning providing an excitation to the sensor coupled to sensor input 23. Such excitation voltage is often used to power and, thus, permit sensing to occur in a variety of different types of sensors, including pressure sensors, as is well known in the art. The sampling and sensing controls are provided by the real time processor 21. Real time processor 21 also drives LED indicator 25 to show the system is running even when the screen is off.

As further seen, this processor is coupled to second non-real time processor 22. Second processor 22 is provided primarily to perform those high processing operations associated with multitasking, graphical user interface, floating point calculation, Infra Red communication and long term memory storage. In particular, the second processor is primarily provided to operate a Windows CE operating system as well as one or more embedded applications, as depicted. As further seen, this processor is coupled to audible buzzer 31 as well as keyboard controls 32, a screen 33 and non-volatile memory 30. Non-volatile memory provides a long term memory for the device such that data can be recorded and preserved even if power is lost. In the preferred embodiment, keyboard controls processes a series of four push buttons, each of which provide one or more different types of system inputs, as provided by the Windows CE™ operating system, available from Microsoft Corporation, Redmond, Washington.

As further seen in this figure, recorder 1 features an infra red port 35 to communicate with the host PC. As depicted in FIG. 1B, the infra red connection permits recorder 1 to receive and exchange data with host PC 10. Host PC, as seen, includes both a Windows 98™ operating system available from Microsoft Corporation, Redmond, Wash., as well as one or more host applications. Host applications permit the treatment of the recorded values and help for diagnostic.

In a preferred embodiment of the present invention the real time processor 21 is a model PIC16LC67 IC from Microchip Technology Inc., Chandler, Ariz.; non-real time processor 22 is a model ElanSC400 IC from Advanced Micro Devices, Inc. Sunnyvale, Calif.; and non-volatile memory 30a model Minicard AMMCL004AWP from Advanced Micro Devices, Inc. Sunnyvale, Calif.

Figure 3:
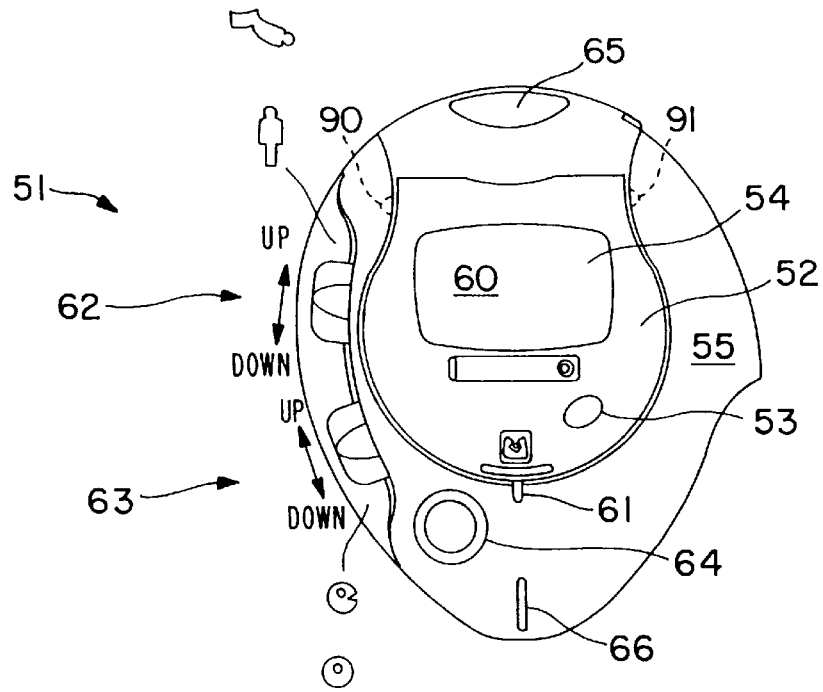
FIG. 3 is a front view of recorder according to the present invention.

FIG. 3 is a front view of recorder 51 according to the present invention. In this view, recorder 51 has its movable front cover 52 closed. As discussed in more detail below, front cover 52 further includes a movable push button shield 53 which allows access to one of the push button controls covered by cover 52 while in the down position. Shield 53, although allowing access to the push button controls, obscures any notation of the push controls button from the viewer when the cover is closed such that a very simplified control interface is presented to any user when the cover 52 is closed. Cover 52 also features transparent window 54 to permit viewing of LCD screen 60 which is integral with recorder 51 (further depicted in FIG. 2). As mentioned, cover 52 may be moved from a closed position, shown in this figure, to an open position, shown in FIG. 4. Movement is controlled by cover catch 61, described in more detail below.

As seen, recorder 51 also features a pair of period switches 62 and 63 which are movable in a linear fashion from a first to a second position. In the preferred embodiment, period switch 62 is a body position switch, and the up position is used to mark periods when the patient is lying down or in a supine position. The down position is used to mark periods when the patient is standing or sitting upright. Period switch 63 preferably is a meal switch and the up position is used to mark a meal period while the down position is used for periods when the patient is not eating. The device further features, an event button 64 which the patient presses to mark events. Such events may include heart palpitations or reflux. Clock button 53, period switches 62 and 63 and event button 64 are all coupled to the keyboard function 32, shown in FIG. 2.

The device further features an infra red data output port having a two plane infra red lens 65. This feature is coupled to the infra red communication block 35 depicted in FIG. 2 and permits the device to communicate, through an infra red connection, to a host PC . The device also features an operation indicator light 66 which would indicate device operation.

Figure 4:
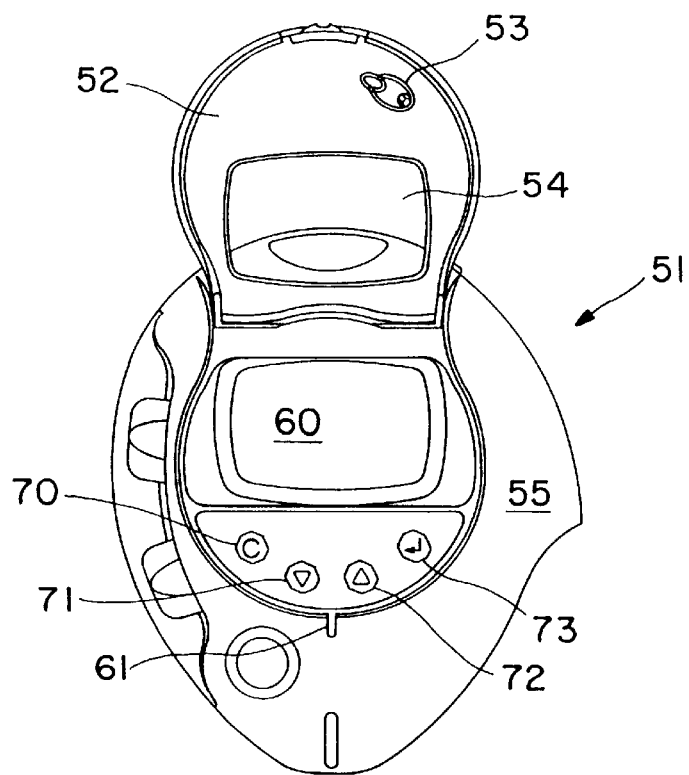
FIG. 4 is a front view of recorder 51 in which cover 52 has been raised.

FIG. 4 is a front view of recorder 51 in which cover 52 has been raised and the device is open. As seen, when open, a series of controls 70, 71, 72 and 73 are exposed. Control 70 is a push button and features, at its front face, the mark C. This control permits the user to return to the previous screen shown on display 60 without having to save any changes. Control 71 is a push button which, in the preferred embodiment, moves the selection bar shown in 60 to the next item down. Control 72 is a push button which, in the preferred embodiment, moves the selection bar to the next item up. Control 73 is, preferably, a push button which executes the current selection in the preferred embodiment.

As seen by a comparison of FIG. 3 and FIG. 4, control push button 73 may be operated regardless of whether the cover is opened or closed during the provision of movable push button 53. An important feature of this shield, however, is that it presents a different notation for the push button when the cover is closed as compared to when the cover is open. As discussed above, past ambulatory recorders have performed less than satisfactorily because too many controls were presented to the patient. While such controls are necessary to be presented to the physician so that the device may be programmed and its operating parameters set in an acceptable manner, such controls are not necessary for the patient when the device is merely recording. Thus, the movable push button shield, mounted to the movable cover, permits the device to provide an enhanced control feature set to a physician while limiting the control feature set for the patient. Cover movement is further controlled by open cover catch 61 which permits the cover to be opened only with a tool, in which in the preferred embodiment is a pen tip. Although not shown in this figure, another feature important to the device operation is that of the hinge point on which the cover is mounted. In the preferred embodiment, the hinge is functionally a break-away hinge such that if excessive force (e.g. greater than eight pounds) is provided to the cover when open it will release from its hinge points without breaking such that it may thereafter be reinserted into its hinge. The breakaway feature is provided in a known manner, such as a deformable polymer cover along with removable hinges, e.g. interlocking hemispherical hinge points and recesses.

Figure 5:
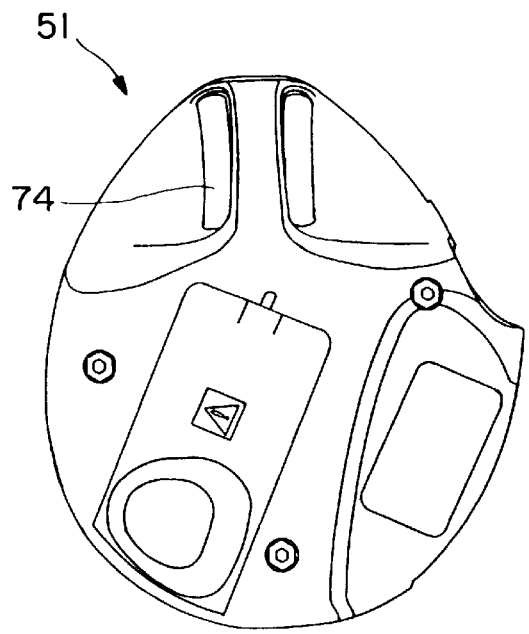
FIG. 5 is a back view of the recorder.

FIG. 5 is a back view of the recorder. As seen, recorder 51 features belt loop 74 which may be used to mount the recorder to a patient using either the patient's belt or the shoulder strap.

Figure 6:
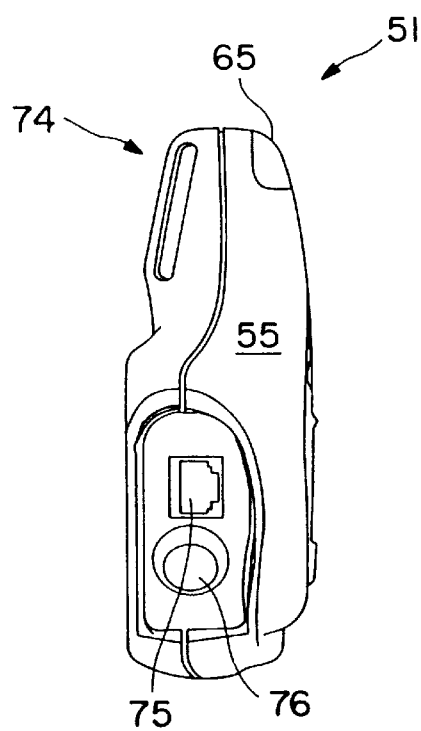
FIG. 6 is a side view of recorder 51.

FIG. 6 is a side view of recorder 51. As further seen in this view, housing 55 features a pair of sensor inputs 75 and 76. In the preferred embodiment, input 75 is for a pH catheter while input 76 is for a pressure measuring catheter. As further seen, recorder 51 features infra red lens 65 which permits an infrared link to a host be made using the IrD communication components shown in FIG. 2. As seen in this view, lens, 65 is positioned along both an upper as well as a side surface of the recorder enclosure. This two sided or multi plane lens thereby permits a large degree of exposure to the internal IrD components inside the enclosure and thus permits an IrD link to be made with the recorder in a variety of positions relative to the IrDA communication device 11 (referring to FIGS. 1A and 1B) Lens 65 may be made of an known standard lens material. In the preferred embodiment lens 65 is made of polycarbonate and the enclosure itself, including the cover, is fashioned from the polymer Crastin™ XMB 850 FR available from E.I. Du Pont De Nemours And Company, Wilmington, Del. The lens, however, should be formed so as to reach across both the upper side as well as front side of the recorder (referring once again to FIG. 6).

Figure 7:
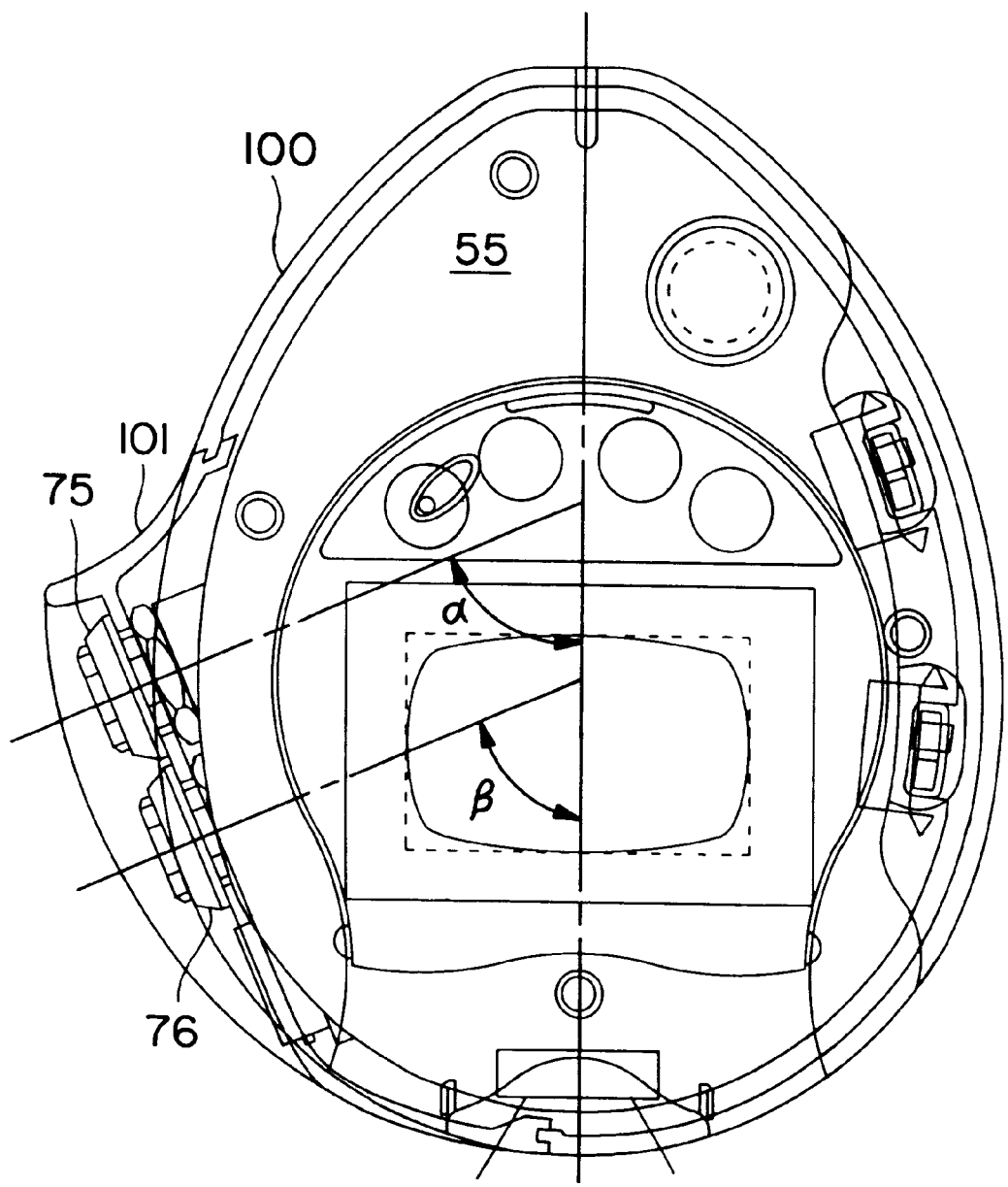
FIG. 7 is a sectional view of the device shown in FIG. 6. and showing the orientation of the ports to the recorder enclosure.

FIG. 7 is a sectional view of the device shown in FIG. 6. As seen, the device features an enclosure 55 having a generally elliptical downward sloping top surface 100. As seen, on at least one side of the device this downward sloping surface 100 merges into a curved shield portion 101. In particular, the downward sloping top surface has an increasing slope until it reverses itself and thereafter forms a surface having a diminishing slope in the region of the curved shield portion. Curved shield portion 101 overhangs sensor ports 75 and 76 when viewed from a vertical orientation, i.e. ports are recessed within housing under the shield portion. Ultimately, top surface 100 and curved shield portion 101 tend to direct any water or fluid falling on the top surface of recorder away from sensor ports. As further seen, sensor ports are disposed at respective angles $\alpha$ and $\beta$ relative to the center line of recorder such that they open in a downward direction relative to both the top surface of the device and the center line of the device. In the preferred embodiment, angles $\alpha$ and $\beta$ are the same and are 67° although they may be anywhere between approximately 0° to at most less than 90°. Through the combination of the downward sloping top surface along with the ports recessed in the shield as well as the downwardly angled ports, an ambulatory recorder may be fashioned in which the sensor ports may be made to be of greater splash resistance than has heretofore been known.

Although various embodiments of the invention have been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. An ambulatory medical data recorder, comprising:
    all enclosure comprising a plurality of exterior surfaces, including opposing front and back exterior surfaces, opposing side exterior surfaces disposed between the front and back exterior surfaces, and opposing upper and lower exterior surfaces disposed between the side exterior surfaces, the enclosure enclosing an interior volume;
    a processor for sampling sensed physiologic data, the processor being disposed within the interior volume;
    at least one sensor port for providing an electrical connection between the processor and an external sensor for sensing at least one physiologic signal, at least a portion of the at least one sensor port being contiguous with at least one of the exterior surfaces of the enclosure;
    sensor port shield, integral or attached to at least one of the exterior surfaces of the enclosure, the sensor port shield extending over at least a portion of the at least one sensor port to prevent the ingress of fluids therein or thereon.

2. The ambulatory recorder of claim 1, wherein the at least one sensor port is contiguous with at least one of the side exterior surfaces of the enclosure.

3. The ambulatory recorder of claim 1, wherein the at least one sensor port is recessed at least partially within the enclosure a second imaginary axis projects through along a major axis of the at least one sensor port.

4. The ambulatory recorder of claim 1, wherein a first imaginary vertical axis is disposed between the front and back exterior surfaces and a second imaginary axis projects through along a major axis of the at least one sensor port, the second imaginary axis forming an angle ranging between about 0 degrees and about 90 degrees in respect of the first imaginary vertical axis.

5. The ambulatory recorder of claim 1, wherein wherein a second imaginary axis forms an angle of about 67 degrees in respect of a first imaginary vertical axis.

6. The ambulatory recorder of claim 1, wherein a first imaginary vertical axis is disposed between the front and back exterior surfaces and a second imaginary axis projects through along a major axis of the at least one sensor port, the second imaginary axis forming an angle that is less than about 90 degrees in respect of the first imaginary vertical axis.

7. The ambulatory recorder of claim 1, wherein wherein the at least one sensor port opens in a downward direction in respect of the upper exterior surface.

8. The ambulatory data recorder claim 1, wherein the sensor port shield is oriented such that it projects downwardly in respect of the upper surface and away from the at least one of the exterior surfaces of the enclosure as the sensor port shield extends over the at least portion of the at least one sensor port.

9. The ambulatory data recorder of claim 1, wherein the sensor port shield forms a curved surface.

10. The ambulatory data recorder of claim 1, further comprising a means for mounting the ambulatory recorder to a patient.

11. The ambulatory data recorder of claim 10, wherein the mounting means comprises a loop configured for a belt or a shoulder strap to be inserted therethrough.

12. The ambulatory data recorder of claim 1, wherein at least one of the side surfaces and the front surface is curved in in a downward direction in respect of the upper surface so as to define a flow path away from the sensor port.

13. The ambulatory recorder of claim 1, further comprising the external sensor.

14. The ambulatory recorder of claim 12, wherein the sensor is a pH catheter.

* * * * *

UNITED STATES PATENT AND TRADEMARK OFFICE
CERTIFICATE OF CORRECTION

PATENT NO.   : 6,119,029
DATED        : August 12, 2000
INVENTOR(S)  : Williams

It is certified that error appears in the above-identified patent and that said Letters Patent is hereby corrected as shown below:

Column 6,
Lines 25 and 35, change "I, wherein, wherein" to -- I, wherein --.
Line 54, change "in in a downward" to -- in a downward --.

Signed and Sealed this

Twenty-fifth Day of March, 2003

JAMES E. ROGAN
*Director of the United States Patent and Trademark Office*